(12) United States Patent
Tada et al.

(10) Patent No.: US 7,631,537 B2
(45) Date of Patent: Dec. 15, 2009

(54) GAS SENSOR

(75) Inventors: Masaki Tada, Osaka (JP); Rihito Shoji, Osaka (JP)

(73) Assignee: Panasonic Corporation, Osaka (JP)

( * ) Notice: Subject to any disclaimer, the term of this patent is extended or adjusted under 35 U.S.C. 154(b) by 54 days.

(21) Appl. No.: 11/578,106

(22) PCT Filed: Mar. 7, 2006

(86) PCT No.: PCT/JP2006/304339
§ 371 (c)(1),
(2), (4) Date: Oct. 10, 2006

(87) PCT Pub. No.: WO2006/095719
PCT Pub. Date: Sep. 14, 2006

(65) Prior Publication Data
US 2009/0133472 A1 May 28, 2009

(30) Foreign Application Priority Data
Mar. 8, 2005 (JP) .............................. 2005-063294

(51) Int. Cl.
*G01N 25/00* (2006.01)
(52) U.S. Cl. .................... 73/23.21; 73/23.31; 73/25.01; 73/25.05; 73/31.05
(58) Field of Classification Search ................. 73/23.2, 73/23.21, 23.31, 23.32, 25.01, 25.03–25.05, 73/9.01, 29.05, 31.05, 31.06, 29.01
See application file for complete search history.

(56) References Cited

U.S. PATENT DOCUMENTS

| | | | | |
|---|---|---|---|---|
| 4,313,338 A | * | 2/1982 | Abe et al. ................... | 73/31.06 |
| 4,896,143 A | * | 1/1990 | Dolnick et al. .............. | 340/634 |
| 4,984,446 A | * | 1/1991 | Yagawara et al. ........... | 73/31.06 |
| 5,151,166 A | * | 9/1992 | Harral et al. ................. | 205/784 |
| 5,551,283 A | * | 9/1996 | Manaka et al. ............. | 73/31.01 |
| 5,621,162 A | * | 4/1997 | Yun et al. ................... | 73/23.34 |
| 5,637,786 A | * | 6/1997 | Weber et al. ............... | 73/23.32 |
| 6,055,849 A | * | 5/2000 | Shioiri et al. .............. | 73/31.06 |
| 6,326,880 B1 | * | 12/2001 | Tice ....................... | 340/286.05 |
| 6,742,382 B2 | * | 6/2004 | Warburton et al. ......... | 73/23.31 |

(Continued)

FOREIGN PATENT DOCUMENTS

JP        4-53574        12/1992

(Continued)

*Primary Examiner*—David A. Rogers
(74) *Attorney, Agent, or Firm*—Wenderoth, Lind & Ponack, L.L.P.

(57) ABSTRACT

A highly accurate gas sensor includes a circuit having an improved S/N ratio. First ends of a heat generating element and reference resistor brought into contact with a detected gas are commonly connected, and second ends are respectively connected to a first switch. The first switch is connected with a power source apparatus for supplying a current to the heat generating element or reference resistor. A voltage measuring portion measures a voltage across the heat generating element or reference resistor. An operating portion switches the first switch between the reference resistor and heat generating element by a predetermined timing by determining a condition of controlling a power source apparatus for supplying at least 3 stages of step-like currents to the heat generating element from the voltage across the reference resistor. A voltage measuring portion measures the voltage across the heat generating element and calculates a concentration of a detected gas.

15 Claims, 4 Drawing Sheets

U.S. PATENT DOCUMENTS

| | | | |
|---|---|---|---|
| 6,916,664 B2* | 7/2005 | Bonne et al. | 436/143 |
| 7,028,530 B2* | 4/2006 | Katsuki et al. | 73/25.03 |
| 7,058,518 B2* | 6/2006 | Shoji | 702/24 |
| 7,360,396 B2* | 4/2008 | Shoji | 73/31.05 |
| 7,481,915 B2* | 1/2009 | Davey et al. | 205/785 |
| 2003/0159497 A1* | 8/2003 | Warburton et al. | 73/23.31 |
| 2005/0066707 A1* | 3/2005 | Katsuki et al. | 73/23.21 |
| 2005/0109081 A1* | 5/2005 | Zribi et al. | 73/31.05 |

FOREIGN PATENT DOCUMENTS

| | | |
|---|---|---|
| JP | 8-101156 | 4/1996 |
| JP | 2000-088674 | 3/2000 |
| JP | 3219855 | 8/2001 |
| JP | 2004-170294 | 6/2004 |
| JP | 2004-191164 | 7/2004 |
| JP | 2004-354210 | 12/2004 |
| WO | WO 2004/106909 A1 * | 12/2004 |

* cited by examiner

GAS SENSOR

TECHNICAL FIELD

The present invention relates to a gas sensor for detecting a concentration of a detected gas mixed with the atmosphere including moisture.

BACKGROUND ART

Recently, a fuel cell attracts much attention, expected and intensively developed as one of measures of resolving an energy or environmental problem. Particularly, a fuel cell using a solid polymer film currently constitutes a main stream of developing a fuel cell since an operating temperature thereof is as low as about 80° C. to be handled easily. However, since the fuel cell uses hydrogen as a fuel, a hydrogen detecting gas sensor is needed as a safety measure against leakage thereof.

In a background art, there is adopted such a gas sensor having a principle of utilizing the fact that a thermal conductivity of hydrogen is extremely larger than that of other gas and detecting a change in a thermal conductivity by presence of hydrogen as a change in a temperature of a heat generating element. According to the gas sensor, when hydrogen is present in air, a heat amount deprived from the heat generating element is larger than that in the case of air, thereby, the temperature of the heat generating element is changed in accordance with a hydrogen concentration. The temperature change is electrically detected as a change in a resistance value of the temperature detecting element.

The heat generating element used in the gas sensor is used also as the temperature detecting element, and as a material, a part thereof a thin film resistor made mainly of platinum is used. Since the thin film resistor is constituted by a thin film, the thin film resistor can be fabricated by utilizing a semiconductor micromachining technology, that is, a micromachining technology. Thereby, an extremely small heat generating element can be formed to provide a characteristic of capable of achieving high speed formation of detection and response of the gas sensor and achieving low power consumption formation.

As reference information with regard to the invention of the application, for example, Japanese Patent Unexamined Publication No. 8-101156 (reference 1) is known.

When the gas sensor is used for detecting leakage of hydrogen, presence of moisture in the detected gas (hydrogen) poses a problem. That is, when moisture is not present, the resistance value of the heat generating element is changed in accordance with the hydrogen concentration. When moisture is present, the resistance value is changed also thereby, and it is difficult to differentiate whether the change is caused by hydrogen or moisture, or a synergistic operation of both.

In contrast thereto, the above-described background art utilizes the fact that by making a current supplied to the heat generating element comprising the platinum thin film resistor variable, an output voltage is changed in accordance with a degree of reaction of the heat generating element. By substituting voltages across both ends of the heat generating element when supplied with the current for a previously calculated estimation equation and simultaneously calculating the voltages, an amount of the atmospheric gas, that is, concentrations of respective gases are calculated from a solution of the estimation equation.

Basically, gas concentrations of a plurality of components can be calculated by such a solving method. However, what poses a problem is a case of detecting a state of leaking hydrogen into the atmosphere in a state in which steam near to 80° C. is substantially saturated as in detecting leakage of hydrogen of a fuel cell. In such a case, when changes in the thermal conductivities of the respective gas components are represented by linear equations as in the background art or fall in ranges regarded to be linear equations, the changes can be calculated by using Chevyshev's orthogonal polynomial.

However, in a system in which steam is conceived to be present by an amount larger than that of hydrogen, a nonlinear property of the mixed system in which the thermal conductivity temporarily rises with moisture and drops after a peak necessarily shows a property having a secondary order or higher degree and therefore, the calculation becomes complicated by simply solving the changes by simultaneously calculating the estimation equation. A plurality of pieces of solutions with regard to moisture are present and the moisture cannot uniquely be determined and therefore, there is brought about a drawback that also the hydrogen concentration cannot uniquely be determined.

In order to overcome such a drawback, the inventors have already proposed the technical thought with regard to a moisture correcting system capable of correcting moisture by utilizing the fact that a heat generating temperature of the heat generating element is made to differ and a difference of outputs of the heat generating element at respective temperatures correspond to moisture by a one-to-one relationship (Japanese Patent Unexamined Publication No. 2004-354210). When a gas sensor is operated by a system of switching a plurality of constant current sources based on the moisture correcting system as described in the reference 1, a detection accuracy of the hydrogen concentration is ±0.5% H2 (% H2 designates hydrogen concentration. same as follows), and the system cannot be regarded necessarily as excellent as a method of detecting the hydrogen concentration of percentage order as in detecting leakage of hydrogen.

The reason is that by correcting moisture, a hydrogen sensitivity becomes small by about one order or more, and an S/N ratio is deteriorated. Therefore, according to the system of switching the constant current sources as described in reference 1, the S/N ratio is increased and the drawback still remains.

DISCLOSURE OF THE INVENTION

The invention provides a highly accurate gas sensor. The gas sensor of the invention includes a heat generating element brought into contact with a detected gas mixed with the atmosphere including moisture, and one end of the heat generating element and one end of a reference resistor are commonly connected. Other end sides of the heat generating element and the reference resistor are connected with a selecting switch for selecting either thereof, and a power source apparatus for supplying a current to the heat generating element or the reference resistor by way of the selecting switch is provided.

A voltage measuring portion for measuring a voltage across both ends of the heat generating element or the reference resistor is provided. An operating portion connected with the selecting switch, the power source apparatus and the voltage measuring portion is provided. The operating portion switches the selecting switch such that a destination of supplying the current from the power source apparatus becomes the reference resistor. The operating portion determines a condition of controlling the power source apparatus for supplying at least three step-like currents having different magnitudes continuously to the heat generating element previously from the voltage across both ends of the reference resistor.

After determining the condition of controlling to supply the three step-like currents to the heat generating element from the voltage across both ends generated across both ends of the reference resistor, the selecting switch is switched from a side of the reference resistor to a side of the heat generating element by a predetermined timing, and the at least three step-like currents having different magnitudes are continuously supplied to the heat generating element by a predetermined time period. Thereafter, the voltage across both ends of the heat generating element after an elapse of the predetermined time period of the heat generating element relative to the respective magnitudes of the currents are inputted to the operating portion and a concentration of the detected gas is calculated and outputted. By the constitution, the currents supplied to the heat generating element by the reference resist or can be adjusted at every time of measurement.

According to the gas sensor of the invention, even when a disturbance factor of a variation in a part of a circuit, or an aging change or a change by temperature or the like is present, the gas sensor can be adjusted to constitute a magnitude of a constant current including the influence and therefore, the gas sensor capable of highly accurately detecting the concentration can be constituted by always supplying a pertinent current to the heat generating element.

Figure 1:
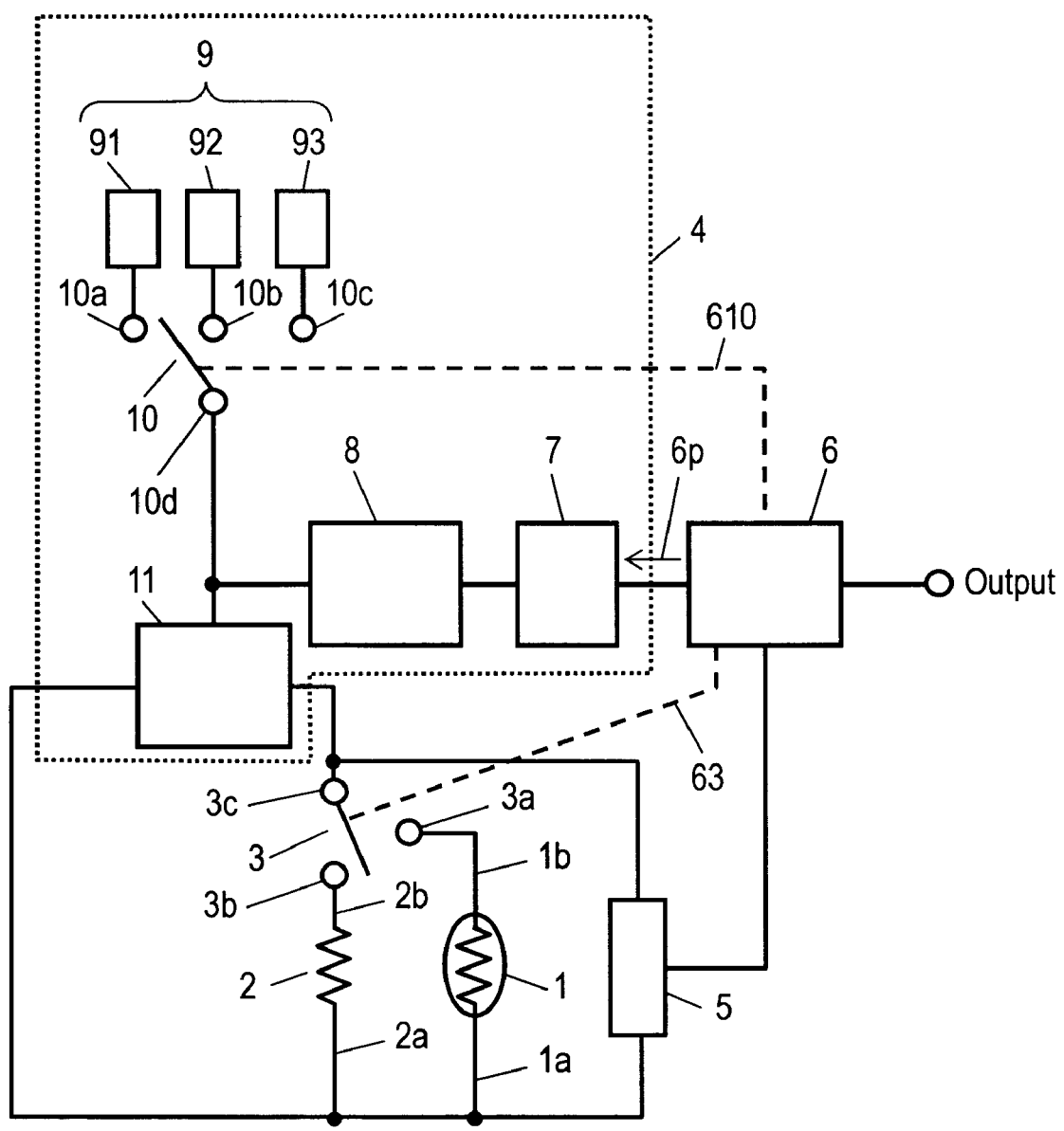
FIG. 1 is a circuit constitution diagram of a gas sensor according to an embodiment of the invention.

DESCRIPTION OF REFERENCE NUMERALS AND SIGNS 1 heat generating element
2 reference resistor
3 first switch
4 power source apparatus
5 voltage measuring portion
6 operating portion
7 amplitude compressing circuit
8 integrator
9 reference voltage generating circuit
10 second switch
11 constant current supplying circuit
91 first reference voltage generating circuit
92 second reference voltage generating circuit
93 third reference voltage generating circuit

BEST MODE FOR CARRYING OUT THE INVENTION

Figure 2:
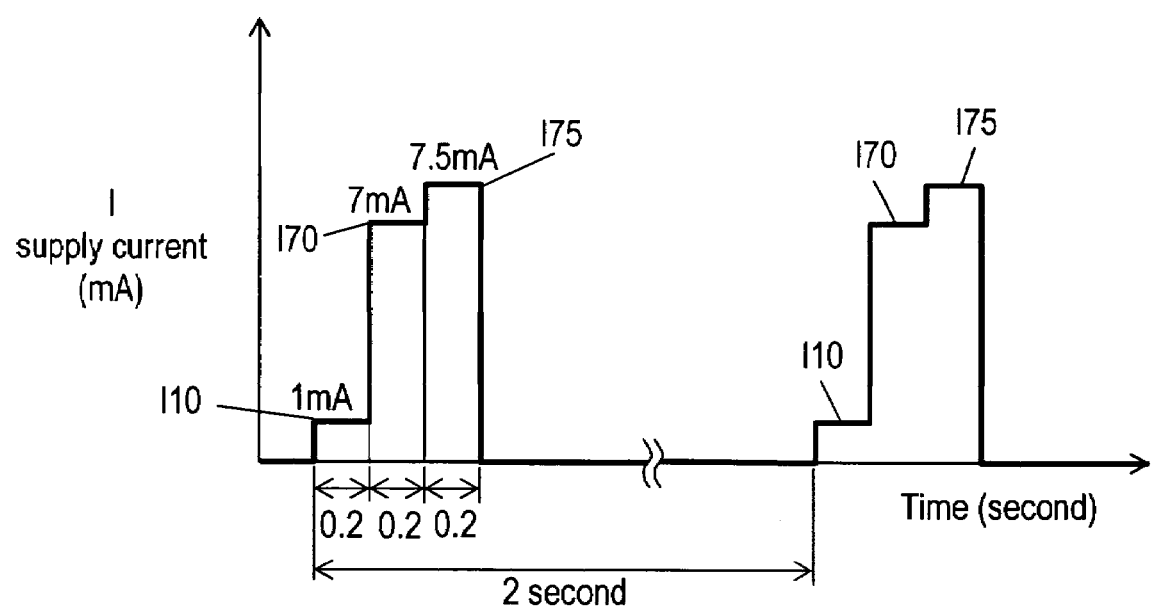
FIG. 2 is a waveform diagram of a current supplied to a heat generating element of the gas sensor according to the embodiment of the invention.
Figure 3:
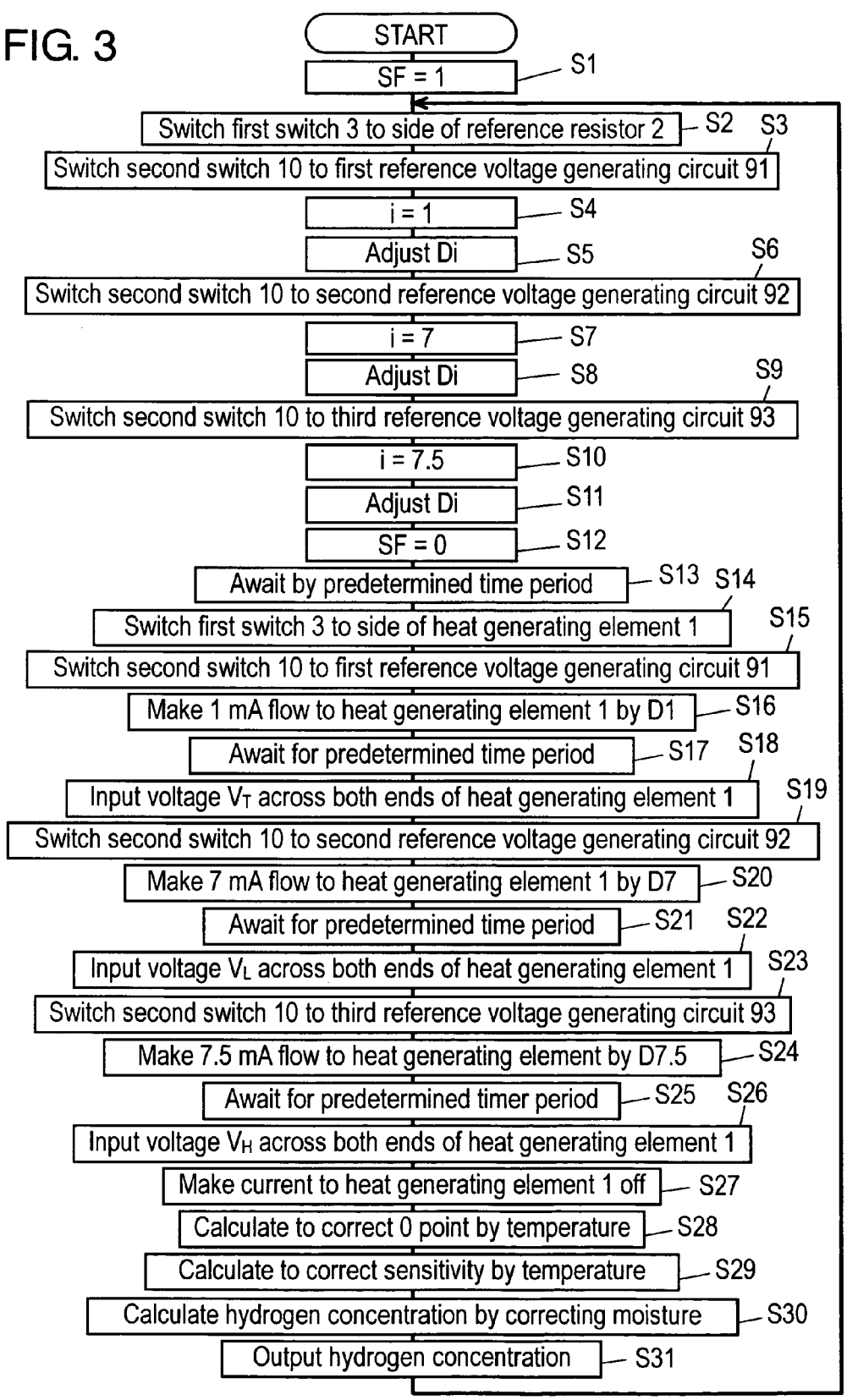
FIG. 3 is a flowchart showing a main operation of the gas sensor according to the embodiment of the invention.
Figure 4:
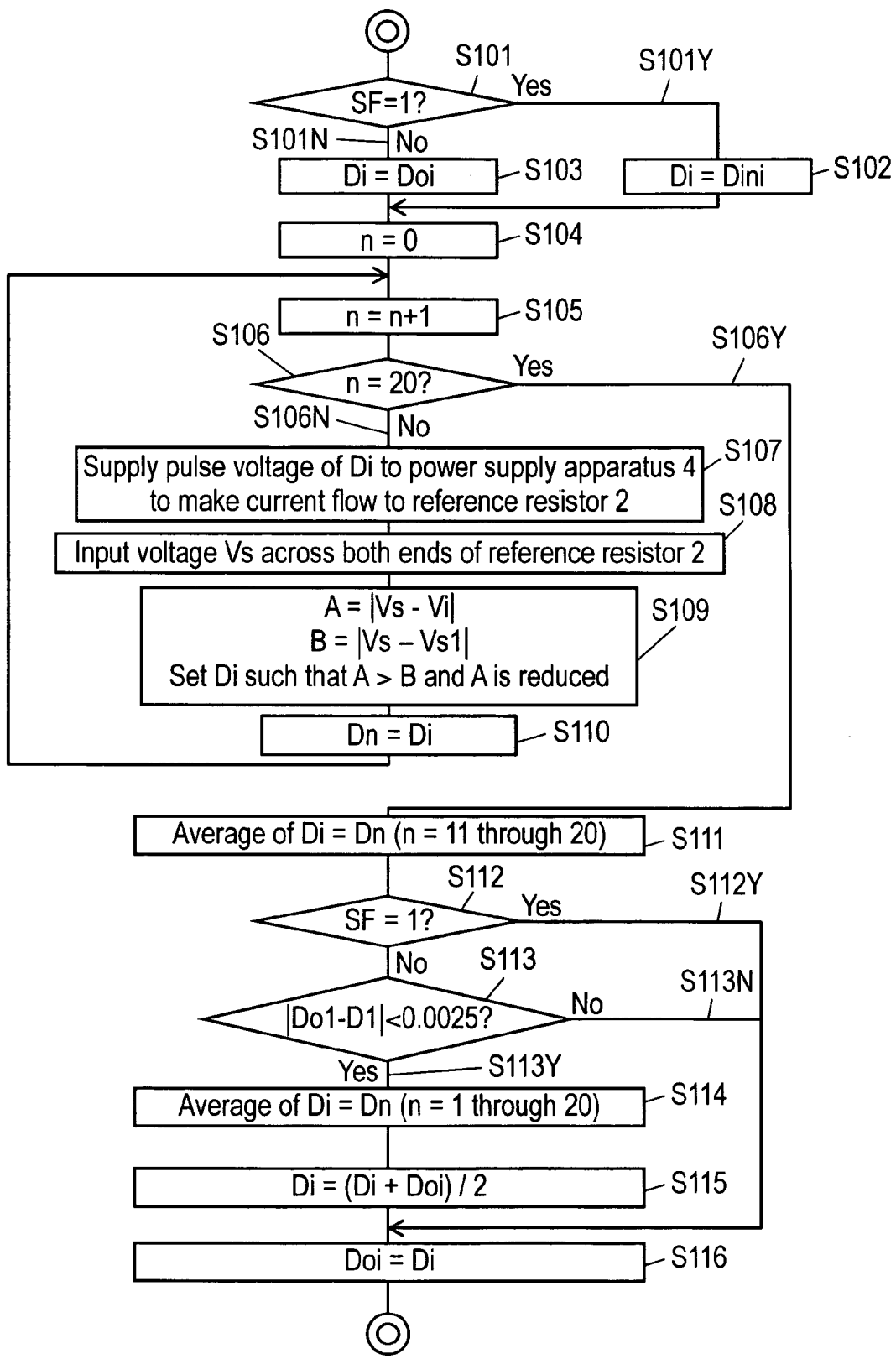
FIG. 4 is a flowchart showing a sub operation of the gas sensor according to the embodiment of the invention.

FIG. 1 is a circuit constitution diagram of a gas sensor according to an embodiment of the invention. FIG. 2 is a wave form diagram of a current supplied to a heat generating element of the gas sensor according to the embodiment of the invention. FIG. 3 is a flowchart showing a main operation of the gas sensor according to the embodiment of the invention. FIG. 4 is a flowchart showing a sub operation of the gas sensor according to the embodiment of the invention.

In FIG. 1, heat generating element 1 for detecting a concentration of a detected gas by being brought into contact with the detected gas mixed with the atmosphere including moisture is constituted by a platinum thin film resistor fabricated by a micromachining technology similar to the constitution of the background art.

According to the invention, an object of a detected gas is constituted by hydrogen having a concentration up to 4% relative to the atmosphere including moisture. A change in a thermal conductivity by hydrogen in the concentration region is to a degree the same as a change in a thermal conductivity by moisture (steam concentration) at 80° C. which is an operating temperature of a fuel cell. Therefore, by constituting the hydrogen concentration region by 4%, according to the invention, an accuracy of detecting the concentration becomes higher than that of the constitution of the background art.

In view of the above-described, an explanation will be given as follows by constituting the hydrogen concentration region of the detected gas by up to 4%.

In FIG. 1, one terminal $2a$ of reference resistor 2 is connected to one terminal $1a$ of heat generating element 1. Reference resistor 2 constitutes a reference in adjusting a current supplied to heat generating element 1 mentioned later and therefore, there is adopted a resistor of a so-to-speak high accuracy product whose temperature change is extremely small as a temperature coefficient representing a rate of a change by temperature of about 5 ppm/° C. Both of resistance values of heat generating element 1 and reference resistor 2 are, for example, about 100 Ω.

Other terminals $1b$, $2b$ of heat generating element 1 and reference resistor 2 are respectively connected with contacts $3a$, $3b$ of first switch 3 for selecting either of the both. Common contact $3c$ of the first switch is connected to contact current supplying circuit 11 constituting a portion of power source apparatus 4 mentioned later. A photoswitch is used for first switch 3. Thereby, an interactive interference brought about between the respective contacts can be excluded and therefore, heat generating element 1 and reference resistor 2 can electrically be insulated sufficiently from each other.

First switch 3 is connected with voltage measuring portion 5 for measuring a voltage across both ends of either one of heat generating element 1 or reference resistor 2. According to voltage measuring portion 5, in order to highly accurately calculate the hydrogen concentration, an AD converter having 19 bits of a voltage inputting accuracy is used to be converted into a digital output.

First switch 3, power source apparatus 4 and voltage measuring portion 5 are respectively connected with operating portion 6. First switch 3 is controlled by operating portion 6 by way of control line 63. A microcomputer having 16 bits or more of an inner operation processing function power is used for operating portion 6. Thereby, an effective column number of operation is increased and a highly precise gas sensor can be realized. A sufficient operation accuracy is achieved by the microcomputer having 16 bits or higher of the processing function power.

Here, power source apparatus 4 will be explained. Power source apparatus 4 converts a ratio of an ON time period to a total of a period within one period of an output signal (pulse voltage) from operating portion 6 (as follows hereinafter abbreviated as duty ratio) into a direct current voltage, produces a constant current in accordance with the direct current voltage and supplies the current to heat generating element 1 or reference resistor 2. The reason that power source apparatus 4 produces the constant current from the duty ratio is that by controlling the current by adjusting the ON time period and an OFF time period of the pulse voltage, the current can highly accurately be controlled by comparatively simple circuit constitution.

Next, a circuit operation procedure of producing the constant current will be explained. First, output signal (pulse voltage) 6P from operating portion 6 is inputted to amplitude compressing circuit 7. Amplitude compressing circuit 7 compresses an amplitude of the pulse voltage by a predetermined rate. By compressing the amplitude of the pulse voltage, in producing the constant current, a current adjusting width, that is, a dynamic range is reduced. However, a resolution of the signal is increased by that amount to be able to finely adjust the current and therefore, the current can highly accurately be controlled.

Next, the signal of the compressed pulse voltage is inputted from amplitude compressing circuit 7 to integrator 8, and the pulse voltage is converted into the direct current voltage. Thereby, a noise component included in the pulse voltage is smoothed and therefore, accuracy of controlling the current is further promoted. In this way, the direct current voltage for finely adjusting the current based on the signal from operating portion 6 is provided.

A gross magnitude of the current supplied to heat generating element 1 or reference resistor 2 is previously determined as a magnitude of the voltage of reference voltage generating circuit 9. Specifically, the power source voltage is determined by dividing a resistor to be able to output the output voltage for setting a magnitude of the current to be supplied.

According to the embodiment, three step-like currents having different magnitudes of currents are supplied to heat generating element 1 as mentioned later. Three of reference voltage generating circuits 9 are prepared to provide gross direct current voltages necessary for producing the respective currents. That is, first reference voltage generating circuit 91, second reference voltage generating circuit 92 and third reference voltage generating circuit 93 are respectively provided successively from the one for supplying the low current.

The three voltages provided at reference voltage generating circuit 9 are switched by second switch 10. Common contact 10d of second switch 10 is connected to constant current supplying circuit 11. Connecting points 10a, 10b and 10c connect first reference voltage generating circuit 91, second voltage generating circuit 92 and third reference voltage generating circuit 93 respectively. Thereby, a gross voltage in correspondence with the magnitude of the current to be supplied is provided to be able to roughly adjust the current to be supplied. Second switch 10 is controlled by operating portion 6 by way of control line 610. A photoswitch is used for second switch 10 by reason the same as that of first switch 3. That is, by using the photoswitch, an interactive interference brought about among contacts 10a through 10c can be excluded.

According to the circuit constitution shown in FIG. 1, a voltage for rough adjustment of reference voltage generating circuit 9 and a voltage for fine adjustment of integrator 8 are provided by signals from operating portion 6 and therefore, a synthesized direct current voltage constituted by adding both voltages can be inputted to constant current supplying circuit 11. In this way, by carrying out rough adjustment and fine adjustment, the current can be adjusted with sufficiently high accuracy even by the microcomputer having the small resolution of the duty ratio.

Constant current supplying circuit 11 supplies the constant current in correspondence with the inputted synthesized direct current voltage to heat generating element 1 or reference resistor 2. Power supply apparatus 4 for controlling the current supplied to heat generating element 1 is formed by such a circuit constitution.

Hydrogen constituting an object of measuring according to the embodiment is present in the atmosphere including moisture and therefore, moisture and a surrounding temperature need to be corrected. Therefore, a basic constitution is constructed by measuring three outputs proportional to a surrounding temperature and in a state in which the voltage across the both ends of heat generating element 1 and a heat generating temperature of heat generating element are made to differ. The voltage across both ends of heat generating element 1 when a low current to a degree by which heat generating element 1 does not generate heat, for example, 1 mA is made to flow substantially represents a magnitude of the surrounding temperature. Therefore, the voltage across both ends at this occasion can be regarded to be an output signal of the surrounding temperature.

As described above, heat generating element 1 is constituted by the platinum thin film resistor fabricated by the micromachining technology. Therefore, a heat capacity thereof is comparatively small. Therefore, in order to make the heat generating temperature differ, the current supplied to heat generating element 1 may be changed. Thereby, a desired temperature can be reached in a time period of several tens milliseconds. When the current is supplied to the platinum thin film resistor within a range in which the resistor hardly generates heat, a voltage output reflecting the surrounding temperature in accordance with a resistance temperature coefficient provided to platinum per se can be provided.

Therefrom, first, by supplying the current to heat generating element 1 by which heat generating element 1 hardly generates heat, an output proportional to a surrounding temperature is provided from the voltage across the both ends. Next, an output at a low temperature is provided by supplying the current constituting a low heat generating temperature. An output at a high temperature is provided by supplying the current constituting a high heat generating temperature. An output only of the hydrogen concentration can be provided by carrying out a predetermined operation from the three outputs.

FIG. 2 shows a waveform of a current supplied to heat generating element 1. The abscissa designates a time period (TIME) of supplying the current, the ordinate designates a magnitude of current I to be supplied, respectively. Heat generating element 1 is applied with pulse currents I10, I70 and I75 by which the current is successively increased. According to the embodiment of the invention, pulse currents I10, I70 and I75 are respectively set to 1 mA, 7 mA and 7.5 mA. As shown by FIG. 2, after successively supplying a step-like current in which three pulse currents having different magnitudes are continuous, heat generating element 1 is cooled to the surrounding temperature by making the current OFF. The voltages across the both ends of heat generating element 1 are respectively inputted to voltage measuring portion 5 to measure magnitudes thereof after an elapse of a predetermined time period after supplying the respective currents. By repeating the operations, the hydrogen concentration at respective periods of the pulse currents can be provided.

As shown by FIG. 2, it is shown that the three pulse currents supplied to heat generating element 1 are successively switched from a current having a low magnitude to a high current. This is because when the current is supplied, a time period of generating heat by heat generating element 1 per se is shorter than a cooling time period, that is, a temperature elevating speed is faster than a temperature lowering speed. Therefore, when the heat generating temperature of heat generating element 1 is elevated in steps, respective desired temperatures can be reached fast and therefore, the period of pulse currents I10, I70 and I75 can be shortened. Thereby, a response of a gas sensor output is accelerated and a highly accurate output instantly in correspondence with a change in the concentration can be provided.

According to the embodiment, the current when the current supplied to heat generating element 1 is the least is set to, for example, 1 mA. It has been confirmed that heat generating element 1 falls in a range in which heat generating element 1 hardly generates heat at the magnitude of the current. Thereby, a change in a heat conductivity by a gas atmosphere at a vicinity of heat generating element 1 is hardly detected and therefore, only the output reflecting the surrounding temperature by the resistance temperature coefficient provided to platinum is highly accurately provided.

The current constituting the low heat generating temperature supplied to heat generating element 1 is set to 7 mA, the current constituting the high heat generating temperature is set to 7.5 mA, respectively. Time periods for supplying 3 stages of the currents are respectively set to 0.2 second, a time period for making the current OFF is set to 1.4 seconds. It has been confirmed that by making the time period of making the current OFF 1.4 seconds, the temperature of heat generating element 1 is sufficiently lowered to room temperature.

According to the embodiment, the pulse current having a period of 2 (0.2×3+1.4=2) seconds is supplied to heat generating element 1. The hydrogen concentration is calculated during a time period of making supply of the current OFF and therefore, the output of the hydrogen concentration is updated at an interval of once per 2 seconds. The hydrogen concentration can be detected by the above-described basic operation.

FIG. 3 shows a main routine operated when the power source of the gas sensor is inputted (i.e., starting a main routine). First, immediately after starting the main routine, at step S1, start flag SF is set to "1".

FIG. 3 shows a main routine operated when the power source of the gas sensor is inputted. First, immediately after starting the main routine, at step S1, start flag SF is set to "1".

Next, at step S2, power source circuit 4 carries out an adjustment for supplying the current of 1 mA to reference resistor 2. Specifically, first switch 3 is switched such that a destination of supplying the current from power source apparatus 4 becomes reference resistor 2. At step S3, by switching second switch 10, first reference voltage generating circuit 91 for rough adjustment is selected.

Next, when the current which is going to be supplied to reference resistor 2 is set to 1 mA, as shown by step S4, i=1 is substituted therefor, a subroutine is executed in order to adjust duty ratio Di at step S5. Here, operation at and after step S6 will be described later and a specific operation will be explained with regard to the subroutine.

FIG. 4 is a flowchart showing the subroutine executed by the gas sensor according to the invention. When the subroutine is executed (START), at step S101, first, a state of start flag SF is investigated, when start flag SF is "1", the operation proceeds to step S102 by way of step S101Y (YES). An operational state at this occasion is constituted immediately after inputting the power source, the set duty ratio is not present and therefore, tentative initial duty ratio Ds previously stored to operating portion 6 is set as current duty ratio Di.

On the other hand, when start flag SF is not "1", the operation proceeds to step S103 by way of step S101N (NO) to set previously set duty ratio Doi as Di. By setting in this way, duty ratio Di is set to a value near to a true value from the start and therefore, a converging time period required for determining the duty ratio in processing of the subroutine is shortened and setting of the duty ratio can highly accurately be adjusted by that amount.

At step S104, even in either processing of step S102 or step S103, a counter value of the number of times n of calculating the duty ratio is set to 0. At step S105, in order to update the number of times n of calculating the duty ratio which is going to be set, the calculating number of times n is added with 1. Next, at step S106, it is determined whether the calculating number of times n becomes 20. When the calculating number of times n does not reach 20, the operation proceeds to step S107 byway of S106N (NO). At step S107, a pulse voltage of duty ratio Di to be set currently is supplied from operating portion 6 to power source apparatus 4. As a result, power source apparatus 4 outputs the constant current in accordance with the voltage constituted by synthesizing the direct current voltage provided from the supplied pulse voltage and voltage of reference voltage generating circuit 9 for rough adjustment.

At step S108, first switch 3 shown in FIG. 1 is switched to reference resistor 2. Therefore, the constant current generated by power source apparatus 4 is supplied to reference resistor 2. As a result, voltage Vs across the both ends in accordance with the magnitude of the constant current is generated across the both ends of reference resistor 2. Voltage Vs across the both ends is inputted to and measured by voltage measuring portion 5.

From voltage Vs across the both ends provided at step S109, a duty ratio for carrying out a successive operating processing is set as Di by the following procedure. First, when set currents to be previously supplied to heat generating element 1, that is, according to the embodiment, three currents having different magnitudes of 1, 7 and 7.5 mA are supplied to reference resistor 2, magnitudes of voltages generated across both ends of reference resistor 2 are previously stored to operating portion 6 as reference voltages Vi (i=1, 7, 7.5). When a highly accurate product having an extremely small temperature coefficient is used for reference resistor 2, regardless of the surrounding temperature of reference resistor 2, reference voltage Vi in correspondence with a magnitude of a target current becomes substantially constant.

Next, there is calculated an absolute value A=|Vs−Vi| of a difference between the voltage Vs across the both ends applied to reference resistor 2 under a current arbitrary environment and the reference voltage Vi stored to calculating portion 6.

Next, in order to reduce the absolute value A, when an absolute value of an amount of a change in voltage Vs1 across both ends of reference resistor 2 which is changed by variably adjusting duty ratio Di is designated by notation B (|Vs−Vs1|), duty ratio Di which is reset such that the latter becomes smaller than the former (A>B), and the magnitude of A per se becomes smaller than the magnitude at a preceding time is set.

By setting in this way, absolute value B by adjusting duty ratio Di becomes always smaller than the difference from absolute value A and therefore, the fine adjustment can be carried out. There can be excluded the drawback that duty ratio Di is deviated from the target and is not converged to the target value, which can be brought about when absolute value B having an adjusting change width larger than that of absolute value A is constituted. By repeating the adjustment, duty ratio Di can highly accurately be set.

When duty ratio Di is set at step S109, after storing duty ratio Di to an alignment Din (n=1 through 20) (S110), the operation returns to step S105 to repeat adjustment of duty ratio Di.

The calculating number of times n for calculating duty ratio Di is set to n=20 according to the embodiment. Generally the larger the number of times, the further highly accurate duty ratio Di is set. Since a processable maximum number of times is 20 times in view of a relationship with a processing speed of the operating portion 6 used in the embodiment, the number of times is used. It can be confirmed that highly accurate formation of a total of the gas sensor is sufficiently achieved by setting the calculating number of times n to 20 times as described later.

It is found that when the calculating number of times n is set to 20 times, the absolute value A=|Vs−Vi| of the difference between voltage Vs across the both ends applied to reference resistor 2 and reference voltage Vi stored to calculating portion 6 can be made to be proximate to substantially 0. It is known that by repeating the operation of calculating duty ratio Di in this way, the voltage Vs across the both ends applied to reference resistor 2 is going to be substantially coincident with reference voltage Vi. Therefore, it is conceivable that by finishing the operation of calculating duty ratio Di at a time point at which the absolute value A becomes substantially 0, duty ratio Di at this occasion may be determined as duty ratio Di at a succeeding time. However, it is known that the operation is insufficient in view of accuracy by the following reason.

That is, when a relationship between absolute value A of the difference between voltage Vs across the both ends applied to reference resistor 2 and reference voltage Vi stored to operating portion 6, and the duty ratio Di is examined in detail, there can be confirmed the fact that absolute value A becomes proximate to 0 certainly before repeating the calculating number of times by 20 times.

However, it is known that duty ratio Di is varied although absolute value A is proximate to 0 in a case of duty ratio Di provided by repeated adjustment thereafter. It is suggested thereby that at every time of adjusting duty ratio Di by which absolute value A becomes proximate to 0, the magnitude is varied since a total of the circuit of the gas sensor is effected with an influence of microscopic noise. Therefore, when the procedure is fixed to a procedure that the duty ratio at a succeeding time is determined only by initial duty ratio Di when absolute value A becomes proximate to 0, final duty ratio Di of the sensor is varied and therefore, output voltages, that is, the voltages across the both ends when respective currents of 1 mA, 7 mA and 7.5 mA are successively supplied to heat generating element 1 are varied and detection accuracy of the gas sensor is deteriorated.

It is found therefrom that the detection accuracy of the gas sensor is promoted when adjustment of duty ratio Di is repeatedly executed by a predetermined number of times, for example, during a time period of 20 times even when absolute value A becomes substantially 0, an average value of respective duty ratios Di is calculated and the calculated average value is set as duty ratio Di at a succeeding time.

The numerical value indicated by a counter reaches 20 at step S106, that is, the calculating number of times n of the duty ratio is finished by an amount of 20 times, the operation proceeds to step S111 by way of step S106Y (YES). At step S111, first, an average value of a later half of a plurality of duty ratios Di of the alignment Din that is, duty ratios Di when the calculating number of times n is 11 through 20 is calculated and the average value is set as duty ratio Di at a succeeding operating processing.

When the processing at step S111 is finished, the operation proceeds to step S112 to investigate a state of start flag SF. When it can be confirmed that start flag SF is "1", the operation is under the state immediately after inputting the power source and therefore, the operation jumps to step S116 by way of step S112Y (YES). In this case, initial value Ds of duty ratio Di is set to a tentative value and therefore, at an initial stage of adjustment, initial value Ds becomes a value remote from a target and when duty ratios Din are averaged by also including duty ratio Din at an initial stage of adjustment, the average value is deviated from a true value of duty ratio Di and an error is increased. In order to avoid the deviation, at step S111, a former half of duty ratios Din having a large change is disregarded, the average value of duty ratios of the later half, that is, in a range of the calculating number of times n of 11 through 20 is calculated and the average value is set as duty ratio Di for succeeding operation.

When start flag SF is not "1", at step S113, it is determined whether an absolute value of a difference between duty ratio Do1 in 1 mA (in Doi, i=1 mA) and duty ratio D1 (in Di, i=1 mA) when a current determined for being supplied to heat generating element 1 is the smallest at a next stage, that is, a change width thereof from that at a preceding time falls in a predetermined range less than 0.0025. When the absolute value does not fall in the predetermined range, the operation jumps to step S116 by way of step S113N (NO). Further, the change width is made to be less than 0.0025 because as a result of various actual measurements according to the embodiment, when the absolute value (change width) of the difference between duty ratio Do1 and duty ratio D1 in the predetermined range is, for example, less than 0.0025, an influence is not effected on final sensor output accuracy.

On the other hand, when the absolute value |Do1−D1| of the duty ratio falls in the predetermined range, the operation proceeds to step S114 by way of step S113Y (YES). At step S114, duty ratio Doi at a preceding time proximate to duty ratio Di at a preceding time proximate to duty ratio Di at a succeeding time which is going to be determined is used as an initial value. Thereby, thereafter, all of a plurality of adjusted duty ratios Din take values proximate to the true value. Therefore, at this occasion, an average value is calculated by averaging a total number (n=1 through 20) of duty ratios Din again to determine as duty ratio Di at a succeeding time and therefore, the current can be supplied stably and highly accurately.

When the average value of the total number of duty ratios Din is calculated, at step S115, an average value is calculated by also averaging duty ratio Di calculated at step S114 and duty ratio Doi determined at a preceding time to determine duty ratio Di used at steps at a succeeding time and thereafter. Thereby, duty ratio Di reflecting duty ratio Doi at a succeeding time is determined.

Thereby, further highly accurate formation can be carried out by excluding a drawback that duty ratio Doi is significantly changed by disturbance noise or the like. At step S113, it is determined that the absolute value of the difference between duty ratio Do1 and duty ratio D1 falls in the predetermined range. This is because since a significant influence is regarded not to be effected from the surrounding temperature in the predetermined range, influence of disturbance noise can be reduced by calculating the average value by averaging a total number of duty ratio Din and calculating the average value by further averaging duty ratio Doi and duty ratio Di.

On the other hand, when deviated from the predetermined range, it can be regarded that the surrounding temperature is rapidly changed and the resistance value of reference resistor 2 is rapidly changed as in immediately after starting the fuel cell and therefore, duty ratio Din and duty ratio Doi can be regarded to be brought in the midst of the change. Therefore, when the average value of the total of duty ratios Din is calculated and the average value of the average value and duty ratio Doi is further calculated, there is brought about a drawback that an error is rather included in duty ratio Di.

Hence, when the absolute value of the difference between the duty ratio Do1 and duty ratio D1 is deviated from the predetermined range, at step S111, the average value of duty ratio Din is calculated at the later half of duty ratio Din brought into a stable state, that is, according to the embodiment, when the calculated number of times n is 11 through 20, the average value is set to succeeding duty ratio Di.

At step S116, duty ratio Doi is updated by substituting duty ratio Di determined to be duty ratio Doi therefor. By the above-described operation, duty ratio Di relative to the target current is determined and the operation returns to the main routine. At step S5, duty ratio D1 for 1 mA is determined and therefore, successively, in accordance with a similar procedure, duty ratios when the current supplied to reference resistor 2 are 7 mA and 7.5 mA are going to be determined.

Here, the operation returns to FIG. 3 again. Steps S1 through S5 have already been explained and therefore, an explanation will be given of step S6 and thereafter.

At step S6, second switch 10 shown in FIG. 1 is switched to select the second reference voltage generating circuit 92 for rough adjustment. Thereby, a preparation of supplying 7 mA to reference resistor 2 is prepared. At step S7, since the current i which is going to be adjusted is 7 mA, i=7 is substituted therefor. Next, the operation proceeds to step S8 to execute the subroutine for adjusting duty ratio Di. Thereby, duty ratio D7 for 7 mA is determined.

At step S8, the subroutine shown in FIG. 4 is executed similar to executing the subroutine at step S5. Further, FIG. 4 has already been described in details and therefore, an explanation thereof will be omitted here.

When the subroutine has been finished at step S8 shown in FIG. 4, the operation proceeds to next step S9. At step S9, a third current supply in 3 stage of supplying the currents to reference resistor 2, that is, according to the embodiment, a final current supply is executed. That is, since the current which is going to be adjusted is 7.5 mA, in order to determine duty ratio D7.5, the second switch 10 shown in FIG. 1 is switched to select third reference voltage generating circuit 93 for rough adjustment.

Next, at step S10, in order to adjust the current i supplied to reference resistor 2 to 7.5 mA, i=7.5 is substituted therefor, at step S11, the subroutine of adjusting duty ratio Di is executed. Thereby, duty ratio D7.5 for 7.5 mA is determined.

At step S12, since respective duty ratios Di constituting a condition of controlling power source apparatus 4 can be determined, next, start flag SF is set to 0. This is because at the time point, initial duty ratio Di has already been determined even immediately after inputting the power source and therefore, the state is no longer immediately after inputting the power source.

In the following, an operation of supplying the currents to heat generating element 1 by determined duty ratio Di is carried out. At step S13, first, the operation is at standby for a predetermined time period in order to match a timing of supplying the currents to heat generating element 1 to every 2 seconds as has been explained in reference to FIG. 2. Next, at step S14, first switch 3 is switched to a side of heat generating element 1. At step S15, second switch 10 is switched to first reference voltage generating circuit 91.

At step S16, the current in accordance with duty ratio D1 determined at step S5 is outputted to power source apparatus 4 and the current of 1 mA is supplied to heat generating element 1. At step S17, the operation is at standby by a predetermined time period. The standby time period is set because even when the current is supplied to heat generating element 1, a desired temperature is not immediately reached. The standby time period is constituted by 0.05 second by adding together a time period of elevating to a desired temperature and a time period until the temperature is stabilized. At step S18, voltage $V_T$ across the both ends of heat generating element 1 is inputted to and measured by voltage measuring portion 5. Since the time period of supplying the respective currents are respectively constituted by 0.2 second and the standby time period at step S17 is 0.05 second, a timing of inputting is taken within a time period of 0.15 second as a difference therebetween.

Voltage $V_T$ across the both ends when 1 mA is supplied to heat generating element 1 can be inputted by the above-described operation. In the following, voltage across both ends $V_L$, $V_H$ are inputted similarly with regard to 7, 7.5 mA.

At step S19, in order to switch second switch 10 to second reference voltage generating circuit 92, second switch 10 is switched to the side of contact 10b.

Next, at step S20, by outputting duty ratio D7 for 7 mA determined at step S8 to power source apparatus 4, the current of 7 mA is supplied to heat generating element 1. Next, after awaiting for a predetermined rectified time period at step S21, at step S22, the voltage $V_L$ across both ends of heat generating element 1 is inputted to voltage measuring portion 5.

Next, at step S23, in order to switch third reference voltage generating circuit 93, second switch 10 is connected to the side of contact 10c. Next, at step S24, the current of 7.5 mA is supplied to heat generating element 1 by outputting duty ratio D7.5 in a case of 7.5 mA determined at step S11 to power source apparatus 4. Next, after awaiting for a predetermined time period at step S25, at step S26, voltage $V_H$ across both ends of heat generating element 1 is inputted to voltage measuring portion 5.

As described above, the continuous 3 stages of the current in the step-like shape is supplied to heat generating element 1 by a predetermined time period and respective voltages across both ends of the heat generating element 1 of $V_T$, $V_L$ and $V_H$ in applied currents of 1, 7 and 7.5 mA are inputted. Thereafter, at step S27, supply of current to the step heat generating element 1 is made OFF.

Next, an operation for calculating the hydrogen concentration is carried out from the inputted voltages across both ends of heat generating element 1 of $V_T$, $V_L$ and $V_H$ in accordance with the following procedure. The respective inputted voltages across both ends become positive integers of 6 digits since voltage measuring portion 5 is constituted by an AD converter having an accuracy of 19 bits. A method of operating the values will be described as follows.

First, at step S28, 0 point correcting operation by a temperature is carried out. Because an object of carrying out 0 point correcting operation resides in that even when the magnitude of the current is assumedly set to be highly accurately, in accordance with a magnitude of each current, the voltage across both ends of heat generating element 1 is changed by the surrounding temperature. 0 point correcting operation is carried out by 0 point correcting equations of Equation 1 through Equation 4 described below.

In Equations 1 through 4, notations $V_{L0}$, $V_{H0}$ designate voltage change amounts of voltages $V_L$, $V_H$ across both ends produced by depending on surrounding temperature T which are brought about at both ends of heat generating element 1 when both moisture and hydrogen are 0%. Voltages across both ends of $V_{ZL}$, $V_{ZH}$ after correcting 0 point show magnitudes constituted by subtracting magnitudes of voltages changed by depending on surrounding temperature T from the voltages across both ends of heat generating element 1, that is, corrected by an amount of the influence of surrounding temperature T. Further, magnitudes of voltages shown below are actually measured values and orders thereof fall in a range of several hundreds mV to several V.

$$V_{L0} = 119715 \times 10^{-14} \times V_T^3 - 771880 \times 10^{-9} \times V_T^2 + 217824 \times 10^{-4} \times V_T + 923398 \times 10^{-1} \quad \text{(Equation 1)}$$

$$V_{H0} = 105074 \times 10^{-14} \times V_T^3 - 646937 \times 10^{-9} \times V_T^2 + 187822 \times 10^{-4} \times V_T + 691799 \times 10^{-1} \quad \text{(Equation 2)}$$

$$V_{ZL} = V_L - V_{L0} \quad \text{(Equation 3)}$$

$$V_{ZH} = V_H - V_{H0} \quad \text{(Equation 4)}$$

Equation 1 is an equation representing a change in 0 point of the voltage across both ends $V_L$ of heat generating element 1 when the heat generating element 1 generates low heat, that is, when 7 mA is supplied depending on the voltage across both ends of $V_T$ when 1 mA is supplied to heat generating element 1. A correlation between voltage $V_T$ across both ends and voltage $V_L$ across both ends in supplying 1 mA to heat generating element 1 when the surrounding temperature is changed in a state in which the concentration of the detected gas is already known in a state in which both of moisture and hydrogen are not present previously is calculated by carrying out third order approximation by a least squares method. Here, third order approximation is carried out because the correlation between voltage $V_T$ across both ends and voltage $V_L$ across both ends can be represented thereby highly accurately.

Therefore, voltage change amount $V_{L0}$ represents an amount of purely changing only by the surrounding temperature T in arbitrary voltage $V_L$ across both ends. When voltage across both ends after 0 point correction of $V_{ZL}=V_L-V_{L0}$ is calculated, an influence of arbitrary surrounding temperature T on voltage $V_L$ across both ends can be corrected.

A coefficient of Equation 1 is displayed by an index having an effective digit of 6 digits and all of inner operation is carried out by an effective digit of 6 digits. This is because as a result of calculation by various effective digits, by 6 digits, a necessary sufficient operational accuracy is achieved as a gas sensor output.

Similarly, Equation 2 is an equation representing a change in 0 point of the voltage across both ends $V_H$ of heat generating element 1 when the heat generating element 1 generates high heat, that is, when 7.5 mA is supplied depending on the voltage across both ends of $V_T$ when 1 mA is supplied to heat generating element 1 and an approximation equation is previously calculated. From Equation 4, an influence on voltage across both ends $V_H$ depending on the arbitrary voltage across both ends $V_T$ can be corrected.

In this way, 0 point correcting operation by temperature is carried out by correcting values of voltages across both ends of $V_L$, $V_H$ of heat generating element 1 from voltage across both ends $V_T$ in correspondence with surrounding temperature T of heat generating element 1 when the current is the smallest in a case of supplying other current.

Next, at step S29, sensitivity correcting operation by temperature is carried out by sensitivity correcting equations based on Equation 5 through Equation 8 by using voltages across both ends after correcting 0 point $V_{ZL}$, $V_{ZH}$.

$$V_{ZL1} = 111933 \times 10^{-11} \times V_T^2 - 353411 \times 10^{-6} \times V_T - 219967 \times 10^{-2} \quad \text{(Equation 5)}$$

$$V_{ZH1} = 632817 \times 10^{-11} \times V_T^2 - 206821 \times 10^{-6} \times V_T - 220734 \times 10^{-2} \quad \text{(Equation 6)}$$

$$KL = V_{ZL}/V_{ZL1} \quad \text{(Equation 7)}$$

$$KH = V_{ZH}/V_{ZH1} \quad \text{(Equation 8)}$$

Here, voltage across both ends for correcting sensitivity $V_{ZL1}$ shown in Equation 5 shows a voltage across both ends of heat generating element 1 at low heat generation, that is, when heat generating element 1 is set to surrounding temperature T and the current of 7 mA is supplied and the concentration of hydrogen is 1%. Above all, a correlation between voltage across both ends $V_T$ in supplying 1 mA to heat generating element 1 in a state in which moisture is not present and when the detected gas including 1% of hydrogen concentration and having a so-to-speak known concentration is brought into contact with the gas sensor according to the invention by carrying out second order approximation by a least squares method. Here, second order approximation is carried out because the correlation between the voltage across both ends $V_T$ and voltage across both ends after correcting 0 point $V_{ZL}$ can be represented highly accurately without carrying out third order approximation.

Similarly, voltage across both ends for correcting the sensitivity $V_{ZH1}$ shown in Equation 6 shows a voltage across both ends of heat generating element 1 in a high heat generation, that is, when heat generating element 1 is set to surrounding temperature T and the current of 7.5 mA is supplied and the concentration of hydrogen is 1%. Above all, a correlation between voltage across both ends $V_T$ and voltage across both ends after correcting 0 point $V_{ZH}$ in a state in which moisture is not present and when the detected gas including 1% of the hydrogen concentration and having a so-to-speak known concentration is brought into contact with the gas sensor is calculated by carrying out second order approximation by a least squares method. Here, second order approximation is carried out because the correlation between voltage across both ends $V_T$ and voltage across both ends after correcting 0 point $V_{ZH}$ can be represented highly accurately without carrying out third order approximation.

Voltages across both ends for correcting sensitivity $V_{ZL1}$, $V_{ZH1}$ shown in Equations 5 and 6 represent output voltages generated at heat generating element 1 when the hydrogen concentration is 1% at surrounding temperature T. Therefore, when arbitrary voltage across both ends after correcting 0 point $V_{ZL}$ is divided by $V_{ZL1}$ to be normalized as shown by Equation 7, an influence of arbitrary surrounding temperature T on voltage across both ends $V_{ZL}$, that is, the influence of the sensitivity can be corrected. Further, ratio KL of voltage across both ends after correcting 0 point $V_{ZL}$ to voltage across both ends for correcting sensitivity $V_{ZL1}$ after correction based on Equation 7 becomes a normalized output of H2 having a unit of %.

Similarly, Equation 6 represents a change in the sensitivity relative to hydrogen when hydrogen concentration is 1% based on voltage across both ends after correcting 0 point $V_{ZH}$ of heat generating element 1 at surrounding temperature T in high heat generation, that is, in 7.5 mA and an approximation equation is previously calculated. Therefore, the influence of the sensitivity of heat generating element 1 on voltage across both ends after correcting 0 point $V_{ZH}$ can be corrected at arbitrary surrounding temperature T based on Equation 8.

In this way, normalized outputs KL, KH are respectively calculated by carrying out sensitivity correcting operation by temperature.

Next, only the hydrogen concentration is calculated at step S30 by correcting for moisture. According thereto, specifically, a moisture correcting equation shown below is used and Equations 9 through 13 are used.

First, normalized output difference Hum of normalized outputs KH and KL is calculated by Equation 9.

$$Hum = KH - KL \quad \text{(Equation 9)}$$

Here, arbitrary normalized output KH is constituted by adding a moisture output to the hydrogen concentration output. Hence, a correlation between normalized output KH and normalized output difference Hum of the detected gas having a known concentration of air including moisture in which hydrogen is not present is previously calculated. As a result, when normalized output difference Hum is calculated from Equation 9, moisture output Off (Off is a value reflecting moisture and therefore, dealt with as moisture output) included in normalized output KH is provided. The inventors have found that normalized output difference Hum is provided with one-to-one correspondence with moisture and therefore, moisture output Off can uniquely calculated from normalized output difference Hum by the property.

Moisture output Off is calculated from Equation 10. Although basically, moisture output Off can be calculated by the correlation with normalized output difference Hum, in order to promote accuracy of calculation, it is necessary to take also an influence of surrounding temperature T which is slightly present into consideration other than normalized output difference Hum. As a result of various investigation by the inventors from the view point, it is found that a correlation between a value of normalized output difference $Hum \times V_T^3$ and normalized output difference Off is the most accurate relative to voltage across both ends $V_T$ relative to normalized output difference Hum and voltage across both ends $V_T$ in supplying 1 mA to heat generating element 1 in correspondence with surrounding temperature T. Equation 10 is a relationship of moisture output Off relative to normalized output difference $Hum \times V_T^3$ representing the excellent relationship.

$$Off = 878551 \times 10^{-53} \times (Hum \times V_T^3)^3 - \quad \text{(Equation 10)}$$
$$193304 \times 10^{-36} \times (Hum \times V_T^3)^2 +$$
$$140458 \times 10^{-20} \times Hum \times V_T^3 + 482210 \times 10^{-7}$$

By substituting for normalized output difference Hum and surrounding temperature T in Equation 10, moisture output Off included in normalized output KH is calculated and therefore, by subtracting normalized output difference Off from normalized output KH as shown by Equation 11, hydrogen output Out is calculated.

$$Out = KH - Off \quad \text{(Equation 11)}$$

Next, a change in the hydrogen sensitivity by moisture of hydrogen output Out is corrected. According thereto, although inherently, an output of only hydrogen is provided by hydrogen output Out, actually the current flows although voltage across both ends $V_T$ thereof is measured by a current condition of generating heat as less as possible when the current of 1 mA is supplied to heat generating element 1, sensitivities of hydrogen and moisture are superposed by slightly generating heat. As a result, a change in the hydrogen sensitivity by moisture is shown. Therefore, in order to provide highly accurate output, also the correction is needed.

As a correcting method, first, inclination HumK of hydrogen output Out relative to respective moistures is previously calculated, and a correlation between inclination HumK and voltage across both ends $V_T$, that is, normalized output difference $Hum \times V_T^3$ in correspondence with moisture in consideration of influence of surrounding temperature T is calculated. The result is shown by Equation 12.

$$HumK = -646500 \times 10^{-54} \times (Hum \times V_T^3)^3 + \quad \text{(Equation 12)}$$
$$763511 \times 10^{-38} \times (Hum \times V_T^3)^2 -$$
$$698337 \times 10^{-22} \times Hum \times V_T^3 + 100255 \times 10^{-5}$$

By substituting normalized output difference Hum and voltage across both ends $V_T$ in Equation 12, hydrogen sensitivity correction value HumK is provided and therefore, by substituting the value in Equation 13, final hydrogen concentration output H2 is provided.

$$H2 = Out/HumK \quad \text{(Equation 13)}$$

Final hydrogen concentration output H2 provided by correcting normalized output KH by Equations 9 through 13 constituting moisture correction equations is outputted as a hydrogen concentration at step S31.

The hydrogen concentration can be continued to be outputted by repeating the above-described stroke as 1 cycle and returning to step S2. The output of the hydrogen concentration is provided at a period of one time per 2 seconds and therefore, the current hydrogen concentration is continued to be outputted until calculating a successive hydrogen concentration. Thereby, the hydrogen concentration can be known at any timing.

When the gas sensor is actually fabricated on trial and evaluated based on the constitution, the accuracy of a total of the gas sensor is ±0.2% H2. This is an accuracy width equal to or smaller than a half of that of the background art and it is confirmed that the gas sensor is suitable for detecting leakage of hydrogen. By executing the circuit constitution, the main routine and the subroutine mentioned above, the highly accurate gas sensor is provided.

Although according to the embodiment, only the hydrogen concentration is outputted, normalized output difference Hum provided by Equation 9 is an output having a correlation with moisture and therefore, a moisture output can also be provided by calculating a correlation between normalized output difference Hum and moisture previously. The surrounding temperature may be outputted by, for example, Celsius unit (° C.) from the value of voltage across both ends $V_T$ of heat generating element 1 as necessary.

According to the embodiment, the step-like currents having three different magnitudes are supplied to heat generating element 1 for detecting hydrogen. However, in a case in which other gas intended to be measured is commonly present, when currents in a step-like shape of 4 stage or more are supplied, concentrations of various gases can be outputted by a similar method.

A specific numerical value described in the embodiment is an example. The invention is not limited to the numerical value of the embodiment, the skilled person can carry out an experiment by variously changing the numerical value within a range of design matter.

INDUSTRIAL APPLICABILITY

The gas sensor according to the invention can provide the highly accurate output by previously adjusting the current supplied to the heat generating element by the reference resistor at each time of measurement and therefore, the invention is useful for being applied to the gas sensor or the like for detecting the concentration and the moisture of the detected gas mixed with the atmosphere including moisture.

The invention claimed is:

1. A gas sensor comprising:
a heat generating element having a first end and a second end, the heat generating element for bringing into contact with a detected gas mixed with an atmosphere including moisture;
a reference resistor having a first end and a second end, the first end of the reference resistor being commonly connected to the first end of the heat generating element;
a switch connected to the second ends of the heat generating element and the reference resistor, the switch for selecting either of the heat generating element or the reference resistor;
a power source apparatus for supplying a current to the heat generating element or the reference resistor by way of the switch;
a voltage measuring portion for measuring a voltage across the first and second ends of the heat generating element or the first and second ends of the reference resistor; and
an operating portion connected with the switch, the power source apparatus and the voltage measuring portion,
wherein the operating portion controls switching of the switch such that a destination of supplying the current from the power source apparatus is the reference resistor,
wherein after determining a condition for controlling the power source apparatus to supply at least three step-like currents having different magnitudes to the heat generating element from the voltage across the first and second ends of the reference resistor, the operating portion controls switching of the switch such that the destination of the current from the power supply apparatus changes from the reference resistor to the heat generating element,
wherein the at least three step-like currents having the different magnitudes based on the determined condition for controlling the power source apparatus are continuously supplied to the heat generating element,
wherein the operating portion receives the voltage across the first and second ends of the heat generating element after an elapse of a predetermined time period for respective current values, and calculates, from equations of correcting a 0 point and a sensitivity previously determined with the voltage across the first and second ends of the heat generating element and a detected gas having a known concentration when a smallest current of the at least three step-like currents is supplied, a normalized output by correcting the voltage across the first and second ends of the heat generating element when each current other than the smallest current of the at least three step-like currents is supplied, and
wherein the operating portion calculates a concentration of the detected gas by correcting each normalized output with a moisture correcting equation previously determined with a difference between the normalized outputs and the detected gas having the known concentration and outputs the calculated concentration of the detected gas.

2. The gas sensor of claim 1, wherein the switch comprises a photoswitch.

3. The gas sensor of claim 1, wherein when the smallest current of the at least three step-like currents is supplied to the heat generating element, the heat generating element hardly generates heat.

4. The gas sensor of claim 1, wherein the at least three step-like currents are set from a low current successively to a high current.

5. The gas sensor of claim 1, wherein the operating portion is a microcomputer having an inner operation processing function of at least 16 bits or more.

6. The gas sensor of claim 1, wherein the operating portion repeats:
controlling switching of the switch such that the destination of supplying the current from the power source apparatus is the reference resistor,
controlling switching of the switch such that the destination of the current from the power supply apparatus changes from the reference resistor to the heat generating element after determining the condition for controlling the power source apparatus to supply the at least three step-like currents having different magnitudes to the heat generating element from the voltage across the first and second ends of the reference resistor,
receiving the voltage across the first and second ends of the heat generating element after the elapse of the predetermined time period for respective current values, and calculating, from the equations of correcting the 0 point and the sensitivity previously determined with the voltage across the first and second ends of the heat generating element and the detected gas having the known concentration when the smallest current of the at least three step-like currents is supplied, the normalized output by correcting the voltage across the first and second ends of the heat generating element when each current other than the smallest current of the at least three step-like currents is supplied, and
calculating the concentration of the detected gas by correcting each normalized output with the moisture correcting equation previously determined with the difference between the normalized outputs and the detected gas having the known concentration and outputting the calculated concentration of the detected gas.

7. The gas sensor of claim 1, wherein the operating portion outputs a pulse voltage and the power source apparatus controls the current supplied to the heat generating element by a duty ratio which is a ratio of a time period that the pulse voltage outputted from the operating portion is on during one period.

8. The gas sensor of claim 7, further comprising an integrator for converting the pulse voltage outputted from the operating portion into a direct current voltage, wherein the current supplied to the heat generating element is controlled by the direct current voltage.

9. The gas sensor of claim 8, wherein an amplitude of the pulse voltage outputted from the operating portion is compressed before being converted into the direct current voltage by the integrator.

10. The gas sensor of claim 9, wherein the current supplied to the heat generating element is controlled by a synthesized direct current voltage constituted by adding the direct current voltage converted by the integrator and a direct current voltage produced by a reference voltage generating circuit.

11. The gas sensor of claim 7, wherein the operating portion stores a voltage generated across the first and second ends of the reference resistor when a target current to be supplied to the heat generating element is supplied to the reference resistor as a reference voltage;

wherein a feedback adjustment for changing the duty ratio is repeated a predetermined number of times such that an absolute value of a difference between the voltage across the first and second ends of the reference resistor and the reference voltage, when the current in accordance with the duty ratio under an arbitrary environment is supplied, is reduced; and wherein after averaging a latter half of a plurality of the duty ratios by a predetermined number of times to set as the duty ratio of a succeeding time relative to the target current, when an absolute value of a difference between the duty ratio when the current is the smallest current at a preceding time and the duty ratio when the current is the smallest current at a succeeding time at other than immediately after starting a main routine falls in a predetermined range, a total number of the plurality of duty ratios are averaged and the average of the total number of the plurality of duty ratios is determined as the duty ratio at the succeeding time.

12. The gas sensor of claim 11, wherein when the duty ratio is adjusted, by adjusting the duty ratio for making the absolute value of the difference smaller than the absolute value of the difference between the voltage across the first and second ends of the reference resistor and the reference voltage stored by the operating portion under an arbitrary environment, the duty ratio is set such that the absolute value of a change amount of the voltage across the first and second ends of the reference voltage is reduced.

13. The gas sensor of claim 11, wherein in adjusting the duty ratio, the duty ratio determined at the preceding time is adopted as an initial value of the duty ratio.

14. The gas sensor of claim 11, wherein in adjusting the duty ratio, when the total number of the plurality of the duty ratios by the feedback adjustment of the predetermined number of times are averaged, the duty ratio at the succeeding time is determined by averaging with the duty ratio determined at the preceding time.

15. A method of detecting a concentration of a detected gas using the gas sensor of claim 1, wherein the detected gas is hydrogen having a concentration up to 4%.

* * * * *